(12) United States Patent
Brumfield et al.

(10) Patent No.: US 6,235,028 B1
(45) Date of Patent: May 22, 2001

(54) SURGICAL GUIDE ROD

(75) Inventors: David L. Brumfield, Southaven, MS (US); Paige A. Myrick, Memphis, TN (US); B. Thomas Barker, Bartlett, TN (US); Troy D. Drewry, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/503,962

(22) Filed: Feb. 14, 2000

(51) Int. Cl.[7] .................................................. A61B 17/56
(52) U.S. Cl. ................................ 606/53; 606/54; 606/57; 606/59
(58) Field of Search .................................. 606/53, 54, 55, 606/56, 57, 58, 59, 60, 61, 69, 70, 71, 72, 73; 623/17.11

(56) References Cited

U.S. PATENT DOCUMENTS

| | | | |
|---|---|---|---|
| 4,913,134 | * 4/1990 | Luque | 606/53 |
| 5,261,909 | 11/1993 | Sutterline et al. | 606/61 |
| 5,411,476 | 5/1995 | Abrams et al. | 604/95 |
| 5,534,002 | 7/1996 | Brumfield et al. | 606/61 |
| 5,551,871 | 9/1996 | Besselink | 433/5 |
| 5,597,378 | * 1/1997 | Jervis | 606/78 |
| 5,637,089 | 6/1997 | Abrams et al. | 604/95 |
| 5,653,710 | 8/1997 | Harle | 606/73 |
| 5,662,648 | * 9/1997 | Faccioli et al. | 606/53 |
| 5,728,097 | * 3/1998 | Mathews | 606/61 |
| 5,797,917 | 8/1998 | Boyd et al. | 606/99 |
| 5,810,817 | 9/1998 | Roussouly et al. | 606/61 |
| 5,899,908 | 5/1999 | Kuslich et al. | 606/96 |

OTHER PUBLICATIONS

*TSRH –3D Surgical Technique*, 1999 by Sofamor Danek, Inc. (Copy to follow.).

* cited by examiner

*Primary Examiner*—Pedro Philogene
(74) *Attorney, Agent, or Firm*—Woodard, Emhardt, Naughton, Moriarty & McNett (57) ABSTRACT

An instrument and method for guiding a spinal implant from a location outside of a patient's body to a location adjacent an exposed portion of a bone anchor engaged to the patient's spine. The instrument is a guide rod having a connecting portion and a guiding portion disposed along a longitudinal axis, with the connecting portion having a shaped end portion adapted to releasably engage a corresponding shaped end portion of the bone anchor. The guiding portion slideably engages a spinal implant and guides the implant along the longitudinal axis until the implant is positioned adjacent the exposed portion of the bone anchor for fixation thereto. The guide rod is then selectively separated or detached from the bone anchor and removed from the patient's body. In one aspect of the invention, the guiding portion is at least partially formed of a malleable material, such as aluminum or a shape-memory material, to allow the guiding portion to be bent or reshaped.

50 Claims, 9 Drawing Sheets

SURGICAL GUIDE ROD

FIELD OF THE INVENTION

The present invention broadly concerns surgical instrumentation. Specifically, the present invention concerns a guide rod for advancing an implant from a location outside the body to a surgical site.

BACKGROUND OF THE INVENTION

Several techniques and systems have been developed for stabilizing and correcting deformities in the spinal column and for facilitating fusion at various levels of the spine. Most of these techniques involve the disposition of a pair of longitudinal elements along opposite sides of the posterior spinal column. The longitudinal elements are engaged to various vertebrae by way of a number of fixation elements to thereby apply stabilizing and corrective forces to the spine.

Typically, the longitudinal element is either a semi-flexible rod or a rigid plate, each having a length sized to span the distance between at least two adjacent vertebrae. A wide variety of fixation elements can be provided which are configured to engage specific portions of a vertebra and connect to a corresponding longitudinal element. For example, one such fixation element is a hook that is configured to engage the laminae of the vertebra. Other prevalent fixation elements include spinal screws or bolts that have a threaded section configured to be anchored in vertebral bone.

If a spinal rod is employed, a series of connector devices are typically used to interconnect the rod to the fixation elements. The connector devices typically have a first opening adapted to receive and engage an upper portion of the fixation element, and a second opening adapted to receive and engage the rod. An example of such a system is the TSRH® Spinal System manufactured and sold by Medtronic Sofamor Danek Group, Inc., the Assignee of the subject application. The TSRH® System includes elongated rods and a variety of hooks, screws and bolts, all configured to create a segmental construct along the spinal column. If a spinal plate is used as the longitudinal element, the plate typically includes a series of openings or slots, through which extends an upper threaded portion of each fixation element. A nut is threaded onto each threaded portion to connect the spinal plate to the fixation elements. An example of such a system is disclosed in U.S. Pat. No. 5,728,097 to Mathews.

The assembly, delivery and manipulation of the implant components described above can be awkward or cumbersome due to the limited amount space available to manipulate the implant components and the required surgical instruments. Additionally, if the openings in the connector devices or spinal plates are not properly aligned with the corresponding upper portions of the fixation elements, considerable force may be required to stress the rod or plate to achieve the alignment necessary to engage the rod or plate to the fixation elements. Moreover, the assembly and manipulation of multiple implant components within the surgical site is tedious and time consuming, thus prolonging the surgical procedure and increasing the risks associated therewith. There is also a risk of mishandling the implant during delivery to the surgical site and possibly dropping the implant within the surgical wound.

There is therefore a general need in the industry to provide surgical instrumentation an techniques for advancing and guiding an implant or implant construct from a location outside of the body to a location adjacent the surgical site. The present invention meets this need and provides other benefits and advantages in a novel and unobvious manner.

SUMMARY OF THE INVENTION

While the actual nature of the invention covered herein can only be determined with reference to the claims appended hereto, certain forms of the invention that are characteristic of the preferred embodiments disclosed herein are described briefly as follows.

In one form of the present invention, a surgical instrument is provided for guiding an implant from a location outside the body to a location adjacent a bone anchor disposed within a surgical site. The instrument comprises a longitudinal member having a connecting portion and a guiding portion. The connecting portion defines an end portion of the longitudinal member and is adapted to releasably engage the bone anchor and being selectively seperable therefrom. The guiding portion is adapted to engage the implant and guide the implant along a length of the guiding portion toward the bone anchor. In a further aspect of the invention, the guiding portion is at least partially formed of a malleable material. In another aspect of the invention, the guiding portion is formed of a shape-memory alloy which may be bent or reshaped into different configurations and selectively returned to its initial configuration.

In another form of the present invention, a method is provided for guiding an implant from a location outside a patient's body to a location adjacent the patient's spine. The method comprises: providing a bone anchor having a bone engaging portion and a guiding portion adapted for releasable connection to the bone engaging portion; anchoring the bone engaging portion to the patient's spine; engaging the implant to the guiding portion and advancing the implant along the guiding portion until positioned adjacent the bone engaging portion; fixing the implant to the bone engaging portion; separating the detachable guiding portion from the bone engaging portion; and removing the detachable guiding portion from the patient's body. In one aspect of the method, the guiding portion is releasably connected to the bone engaging portion after anchoring the bone engaging portion to the patient's spine. In another aspect of the method, the guiding portion is bent prior to advancing the implant along the guiding portion.

It is one object of the present invention to provide a surgical instrument and method for guiding a spinal implant from outside the body to a location adjacent the spinal column.

Further objects, features, advantages, benefits, and aspects of the present invention will become apparent from the drawings and description contained herein.

BRIEF DESCRIPTION OF THE DRAWINGS

FIG. 1b is an end view of the guide rod assembly of FIG. 1a.

FIG. 1c is a cross sectional view of the guide rod assembly of FIG. 1a taken along line 1c—1c.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, any alterations and further modifications in the illustrated devices, and any further applications of the principles of the invention as illustrated herein being contemplated as would normally occur to one skilled in the art to which the invention relates.

Figure 1A:
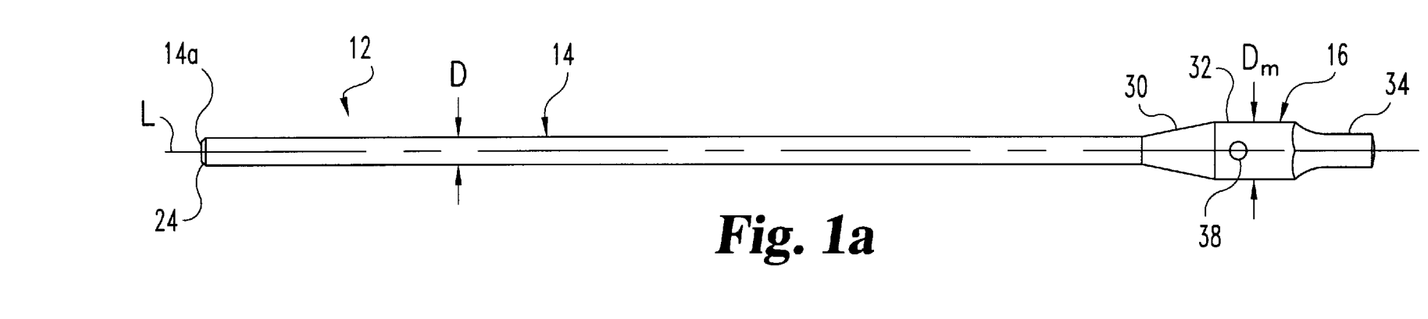
FIG. 1a is a side elevation view of a guide rod assembly according to an embodiment of the present invention.
Figures 1B, 1C:
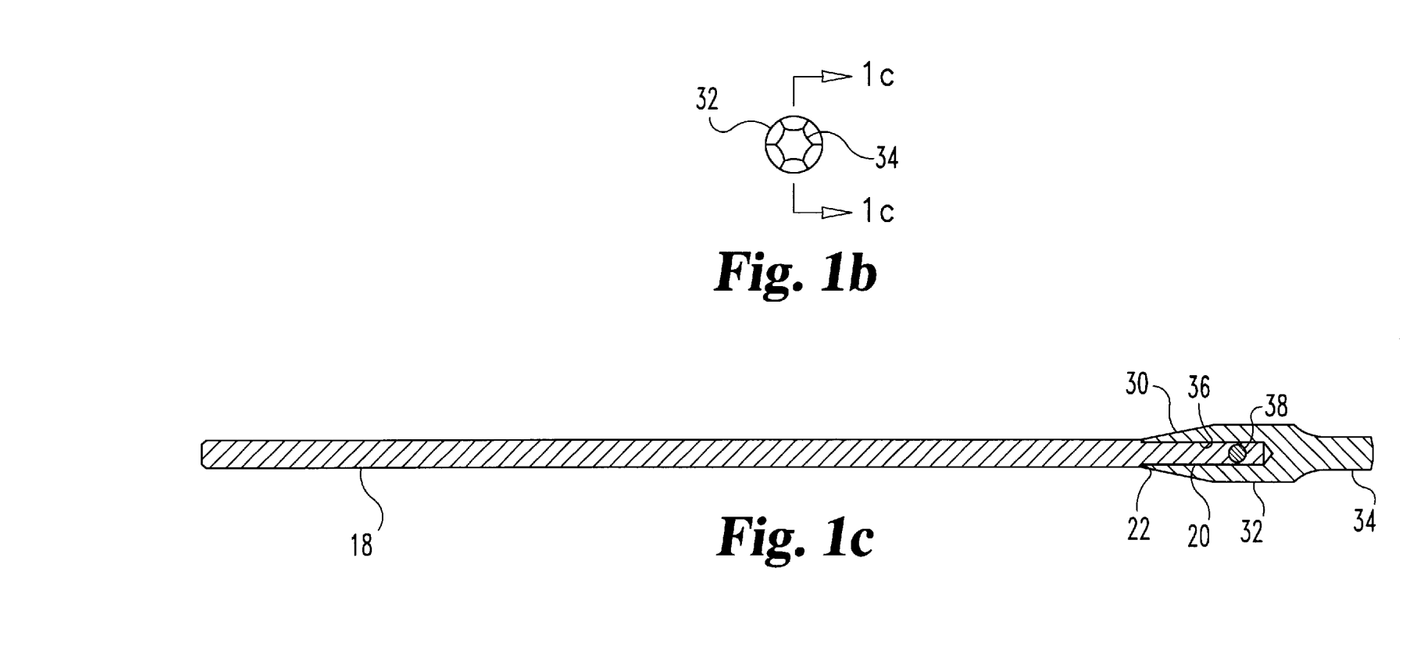

FIGS. 1a–1c depicts a guide rod assembly 12 according to one embodiment of the present invention. Guide rod assembly 12 has a longitudinal axis L extending along an elongate guiding portion 14 and a connecting portion 16. The guiding portion 14 is adapted to slidably engage an implant, and the connecting portion 16 is adapted to releasably engage a bone anchor so that the implant may be guided along the longitudinal axis L from a location outside a patient's body to a location adjacent a bone anchor engaged to bone. Further details regarding the instrument and method for guiding the implant are set forth below.

The elongate guiding portion 14 includes a main body portion 18, having an outer diameter D, and an attachment portion 20 having an outer diameter sized slightly smaller than D so as to define an annular shoulder 22. The distal end 14a of the guiding portion 14 defines a taper 24. In one embodiment of the invention, the guiding portion 14 is at least partially formed of a substantially malleable or pliable material, such as, for example, an aluminum material, a shape-memory material, or any other material capable of being bent or reshaped into different configurations, such as a plastic material or certain compositions or formations of stainless steel or titanium. If an aluminum material is used, the guiding portion 14 is preferably covered with a protective coating such as an anodized oxide film or at least one layer of an elastomeric polymer, such as, for example, Teflon. The use of a malleable material allows the guiding portion 14 to be reshaped or bent into a number of different configurations suitable for guiding an implant along the longitudinal axis L. Preferably, the malleable material allows the surgeon to bend the guiding portion 14 manually by hand.

In another embodiment of the invention, the guiding portion 14 is formed of a non-malleable material, such as, for example, certain compositions or formations of stainless steel or titanium. The use of a non-malleable material allows the guiding portion 14 to be pre-shaped or pre-bent into a predetermined configuration suitable for guiding an implant along the longitudinal axis L. The use of a non-malleable material also provides sufficient strength and rigidity to the guiding portion 14 to manipulate a bone anchor or other devices within the surgical site.

If the guiding portion 14 is at least partially formed of a shape-memory alloy (SMA), the guiding portion 14 can be bent or reshaped from an initial configuration to a different configuration suitable for guiding an implant along the longitudinal axis L, and is capable of being returned to its initial configuration without having to manually bend the guide rod back to its original shape. This shape-memory characteristic occurs when the SMA is transformed from a martensitic crystal phase to an austenitic crystal phase. As will be discussed below, this phase transformation can occur with or without a corresponding change in temperature.

The shape of an article formed of a SMA is "preprogrammed" at a temperature well above the transformation temperature while the SMA is in its austenitic state. When sufficiently cooled to a temperature below the transformation temperature, the article will transform to its martensitic state and the SMA will become relatively weak and pliable, thus allowing the article to be easily reformed or reshaped into different shapes and configurations. This increased malleability or pliability occurs due to the formation of temperature-induced martensite, and when the SMA is subsequently heated to a temperature above its transformation temperature, the SMA will revert back to its austenitic state and the article will return to its original, preprogrammed shape. Further details regarding this shape-memory phenomena and additional characteristics of temperature-induced martensite are more fully described in U.S. Pat. No. 5,551,871 to Besselink, entitled "Temperature-Sensitive Medical/Dental Apparatus", the contents of which are hereby incorporated by reference.

Additionally, some SMAs are known to display a super-elastic phenomena, occurring due to the formation of stress-induced martensite (SIM). When an SMA article exhibiting SIM characteristics is stressed or deformed at a temperature above the transformation temperature, the SMA first deforms elastically. Upon the further imposition of stress, the SMA begins to transform into its martensitic state where the SMA exhibits super-elastic properties. When the stress is removed from the article, the SMA will revert back into its austenitic state and the article will return to its original, pre-programmed shape, all occurring without a corresponding change in temperature. Further details regarding this super-elastic phenomena and additional characteristics of stress-induced martensite are more fully described in U.S. Pat. No. 5,597,378 to Jervis, entitled "Medical Devices Incorporating SIM Alloy Elements", the contents of which are hereby incorporated by reference.

There is a wide variety of shape-memory materials, including shape-memory metal alloys (e.g., titanium based alloys and iron based alloys) and shape-memory polymers, each having a wide range of possible transformation temperature ranges. Selection of an appropriate shape-memory material will depend, in large part, on the required material properties for the particular application and working environment of the device. While there are many alloys that exhibit shape-memory characteristics, one of the more common SMAs is an alloy of nickel and titanium. One such alloy is nitinol, a bio-compatible SMA of nickel and titanium. nitinol is well suited for the particular application of the present invention because it provides a transformation temperature somewhat above normal human body temperature. Moreover, nitinol has a very low corrosion rate, which provides an advantage when used within the human body. Additionally, implant studies in animals have shown minimal elevations of nickel in the tissues in contact with the nitinol material.

If the guiding portion 14 is at least partially formed of a SMA, pre-programmed to have a substantially straight, original configuration, and is later reshaped or deformed while at a temperature below the transformation temperature, the guiding portion 14 will return to its original configuration when heated to a temperature above the transformation temperature of the SMA. Alternatively, if the guiding portion is 14 is reshaped or deformed through the imposition of stress while at a temperature above the transformation temperature, the guiding portion 14 will return to its original configuration when the stress is removed. Deciding which of these phenomena is most appropriate for a given application primarily centers around the degree of pliability required to reshape guiding portion 14, and whether the deformed shape is required to be maintained during the implant procedure.

The connecting portion 16 includes a tapered portion 30, a central portion 32, and a shaped end portion or stem 34. A longitudinal cavity 36 extends through tapered portion 30 and partially through central portion 32. The attachment portion 20 of guiding portion 14 is inserted within the cavity 36 and the end of the tapered portion 30 is engaged against the annular shoulder 22. A cross pin 38 is inserted through a transverse opening 40 extending through the attachment portion 20 and the central portion 32 to securely attach the guiding portion 14 to the connecting portion 16. Other methods of attaching guiding portion 14 to connecting portion 16 are also contemplated, such as, for example, by welding, threading or crimping. Additionally, although a separate guiding portion and connection portion are shown for purposes of illustration, it is contemplated that the entire assembly may be formed of a single piece of material.

In the illustrated embodiment, the central portion 32 has a maximum outer diameter $D_m$ and the tapered portion 30 provides a smooth transition between the outer diameter D of the main body portion 18 and the maximum outer diameter $D_m$. The shaped end portion 34 preferably has a hexagonal shape; however, other shapes are also contemplated as being within the scope of the invention. For example, the shaped end portion 34 could alternatively have a circular, elliptical or square shape, or could take on a number of other geometric shapes, such as a Torx™ type male drive configuration. It is also contemplated that the shaped end portion 34 may include external threads for engagement with a corresponding internal thread.

Figure 2:
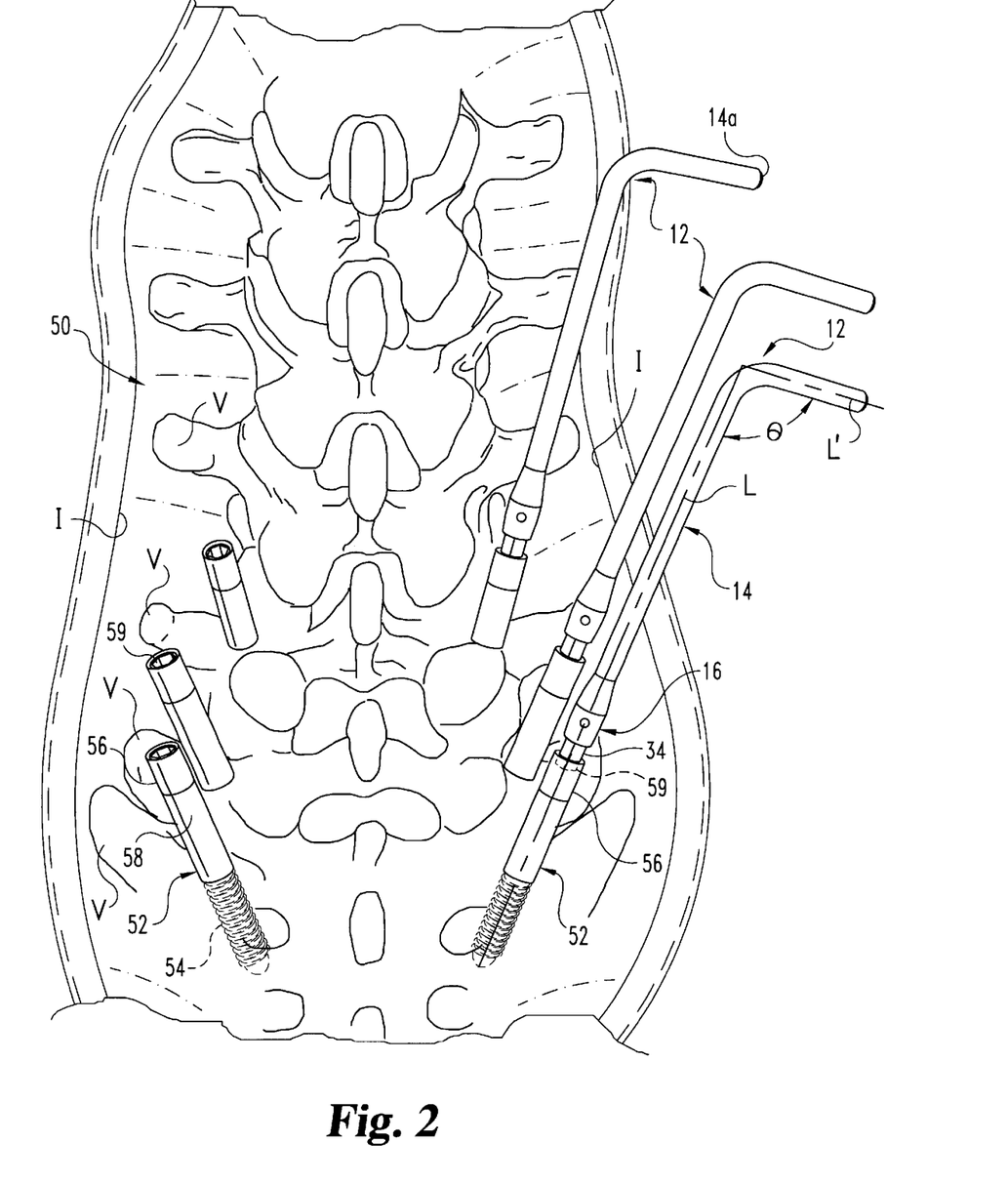
FIG. 2 is a posterior view of a vertebral column showing a number of bone screws attached thereto along each side of the vertebral column, and a series of guide rod assemblies engaged to an exposed end portion of the bone screws.
Figure 3:
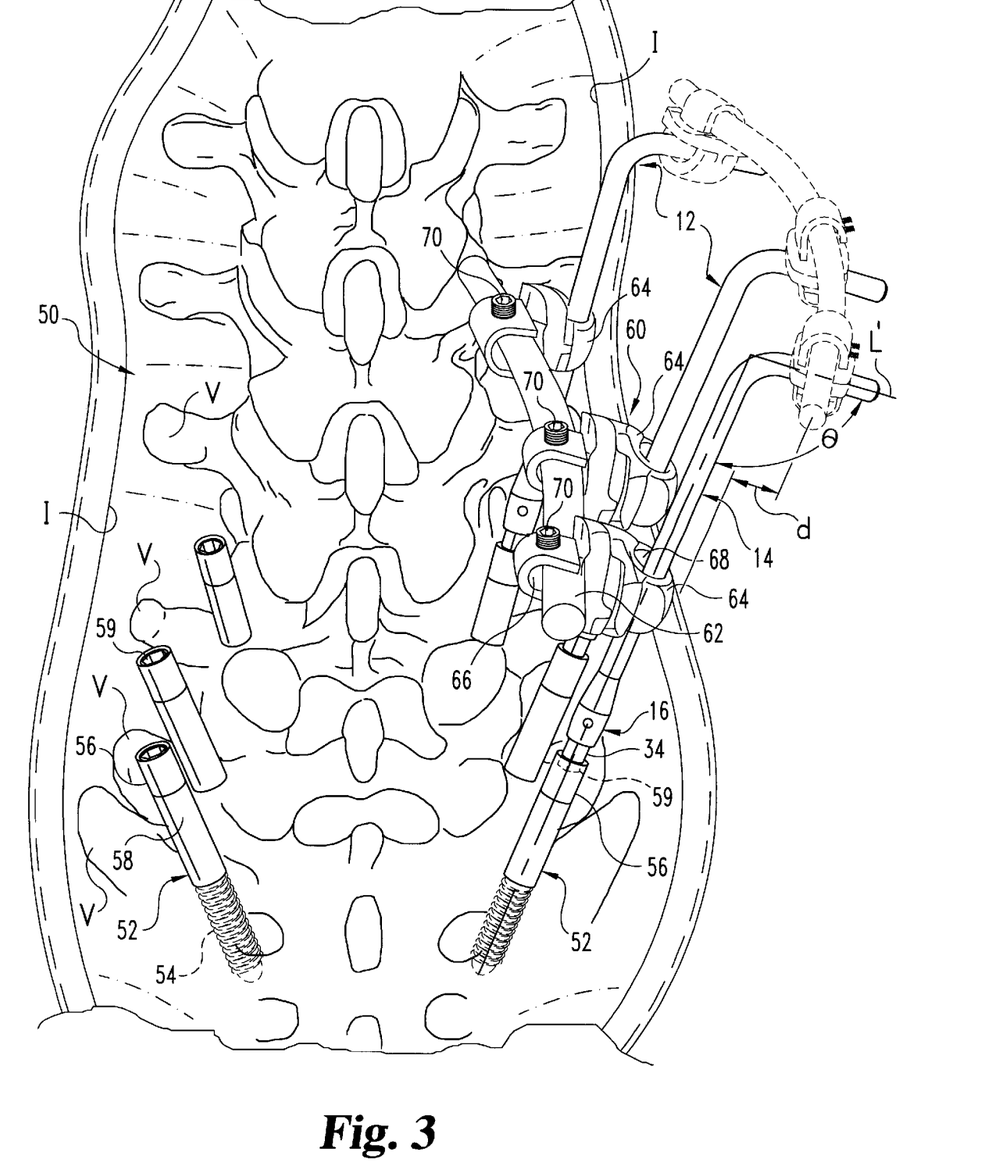
FIG. 3 is a posterior view of the vertebral column, showing a spinal rod/connector construct engaged to the series of guide rod assemblies and being guided toward the exposed end portions of the bone screws.
Figure 4:
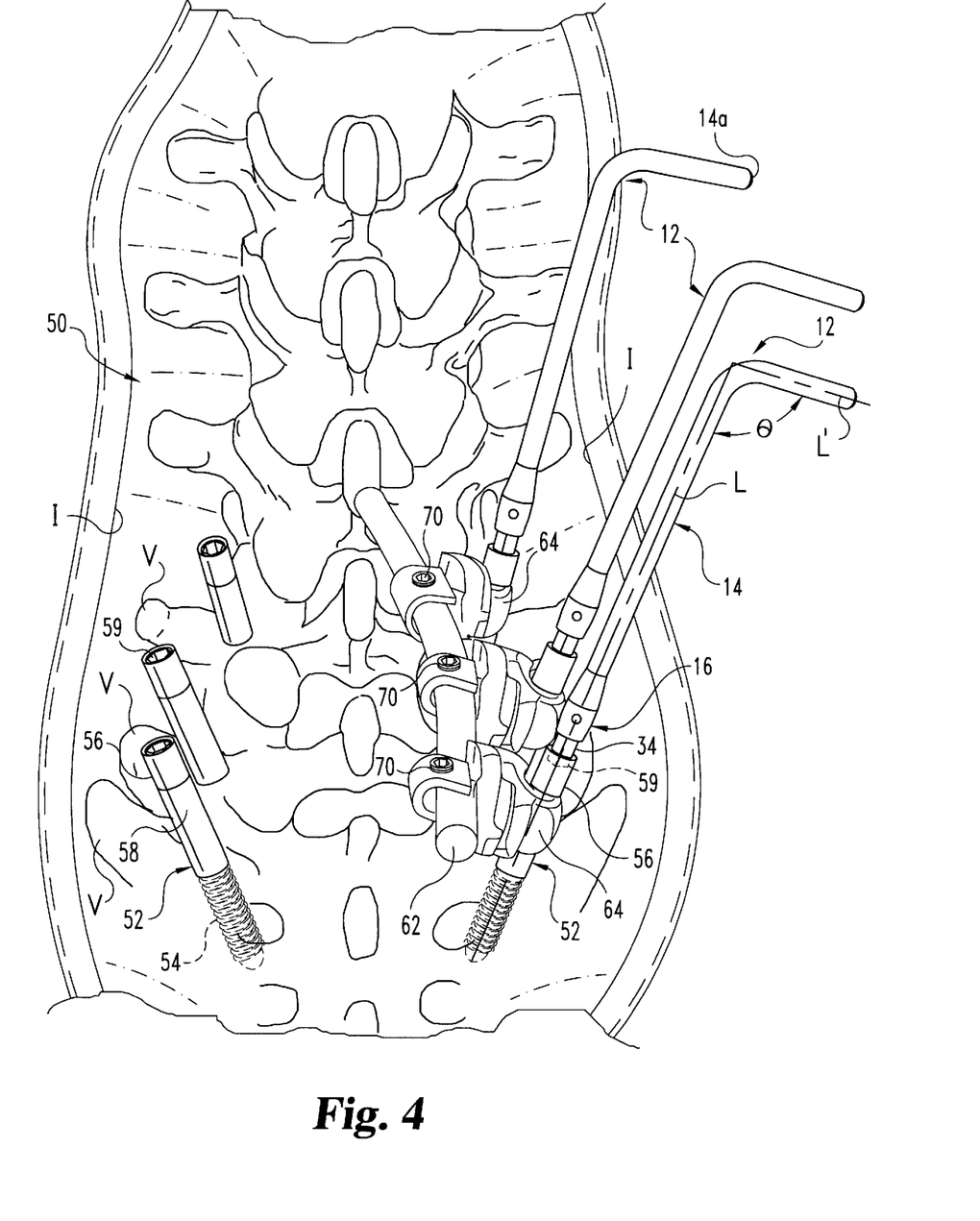
FIG. 4 is a posterior view of a vertebral column, showing the spinal rod/connector construct engaged to the bone screws.

Referring now to FIGS. 2–4, shown therein is the guide rod assembly 12, as used in one embodiment of a method for guiding an implant from a location outside a patient's body to a location adjacent the patient's spine. Referring specifically to FIG. 2, shown therein is a surgical incision I made posteriorly along the patient's spine, exposing a posterior view of the vertebral column 50 comprised of a plurality of vertebrae V. A number of bone anchors 52 are engaged to adjacent vertebrae V along each side of the vertebral column 50. In the illustrated embodiment, the bone anchors 52 are bone screws; however, other types of bone anchors are also contemplated as would occur to one of ordinary skill in the art. For example, the bone anchors 52 could be spinal hooks configured to engage a specific portion of a vertebra, such as the laminae. An example of spinal hooks configured to engage the vertebral column is disclosed in U.S. Pat. No. 5,534,002 to Brumfield et al., the contents of which are hereby incorporated by reference.

Each of the bone screws 52 includes a distal threaded portion 54 anchored in a corresponding vertebra V and a proximal shank portion 56 extending from the threaded portion 54 above a posterior surface of the vertebra. The bone screw 52 is preferably a self-tapping pedicle screw having cancellous threads defined on threaded portion 54 and configured to engage vertebral bone. The shank portion 56 defines a generally circular outer surface 58, and is devoid of any sharp corners or edges which might otherwise irritate adjacent tissue. In one embodiment, the shank portion 56 also defines a shaped opening or recess 59 corresponding to the shaped end portion 34 of the guide rod assembly 12. In the illustrated embodiment, the shaped recess 59 has a hexagonal shape; however, other shapes are also contemplated as being within the scope of the invention. For example, the shaped recess 59 could alternatively have a circular, elliptical or square shape, or could take on a number of other geometric shapes, such as a Torx™ type female drive configuration. It is also contemplated that the shaped recess 59 may include internal threads for engagement with a corresponding external thread defined on the connecting portion 16 of guide rod assembly 12.

A series of guide rod assemblies 12 are engaged to the bone screws 52 which are securely anchored along the right side of the vertebral column 50. More specifically, the hexagonally-shaped end portion 34 of connecting portion 16 is inserted within the hexagonally-shaped recess 60 of shank portion 56 to thereby releasably engage or connect each guide rod assembly 12 to a corresponding bone screw 52. It should be understood that the shank portion 56 of the bone screw 52 could alternatively define a hexagonally-shaped end portion which is insertable within a hexagonally-shaped recess defined in the connecting portion 16 of guide rod assembly 12.

In one embodiment of the invention, the bone screws 52 are implanted or anchored to the vertebral column 50 prior to connecting or joining the guide rod assemblies thereto. It is also contemplated that the bone screws 52 and the guide rod assemblies 12 may be interconnected prior to insertion into the patient's body. The guide rod assemblies 12 effectively serve to extend the length of the shank portion 56 of the bone screws 52. Preferably, the distal end 14a of each guide rod assembly 12 extends outside of the patient's body beyond the surgical incision I when the guide rod assembly 12 is engaged to a corresponding bone screw 52. However, it is also contemplated that the distal end 14a can be positioned below the surgical incision I, while still allowing the guide rod assembly 12 to effectively extend the overall length of the bone screws 52. Notably, the guide rod assembly 12 can be selectively detached or separated from the bone screw 52 by simply removing the shaped end portion 34 from the shaped recess 60.

In the illustrated embodiment, the guide rod assemblies 12, and more specifically the guiding portions 14, are bent laterally outward relative to spinal column 50, with the distal or upper portion of the guiding portion 14 defining a longitudinal axis L' being disposed at an angle θ relative to the longitudinal axis L of the proximal or lower portion. In one embodiment, angle θ is approximately 90°, with the upper portions of guiding portions 14 being disposed substantially parallel to the surface of the operating table (not shown) to form a type of loading rack, thus allowing a spinal implant to be loaded onto the guide rod assemblies 12 from a location laterally remote from the surgical incision I. However, it should be understood that angle θ can be varied to accommodate other types of loading arrangements. It should also be understood that the guiding portions 14 can be substantially straight or reshaped or bent into other configurations. For example, the guiding portion 14 could be bent along the longitudinal axis L to form an arcuate or curved shape to accommodate various types and configurations of spinal implants.

Referring to FIG. 3, shown therein is a spinal implant 60 engaged to the guiding portions 14 of the series of guide rod assemblies 12. In the illustrated embodiment, implant 60 is a spinal rod/connector construct, including an elongated spinal rod 62 and a plurality of connector assemblies 64 attached thereto. The spinal rod 62 has a generally circular outer cross section and has a length sized to span the distance between at least two adjacent vertebrae V. Each connector assembly 64 has a first opening or passage 66 sized to slidably receive the spinal rod 62 therethrough, and a second opening or passage 68 oriented substantially perpendicular to the first opening 66 and sized to slidably receive the shank portion 56 of bone screw 52 therein. Each connector assembly 64 also includes a set screw 70 engaged within a threaded opening intersecting first opening 66.

In the illustrated embodiment, implant assembly 60 is the TSRH 3D® Spinal System manufactured and sold by Medtronic Sofamor Danek Group, Inc., the Assignee of the subject application. Further details regarding the TSRH 3D® Spinal System are more fully described in a product brochure entitled "TSRH-3D Surgical Technique", published in 1999 by Sofamor Danek, Inc., the contents of which are hereby incorporated by reference. It should be understood, however, that the precise configuration of the implant assembly 60 and the bone screws 52 are for illustration purposes only, and that other configurations are also contemplated as being compatible for use with the present invention.

In one embodiment of the invention, the assembly of the implant assembly 60 is performed external of the patient's body prior to being inserted into the patient's body (as shown in phantom lines). In one aspect of the invention, the implant assembly 60 is assembled at a location laterally offset from the surgical incision I at a distance d. Assembly outside the body is typically easier and less complicated than if performed internally due to severe space limitations within the surgical site. Moreover, the assembly and manipulation of implant components outside of the body may reduce the amount of time spent in surgery, thereby reducing the risks associated therewith. Additionally, assembly at a location laterally offset from the surgical site reduces the risk of mishandling the implant components during delivery or assembly and possibly dropping the components into the patient's body.

Each of the connector assemblies 64 are engaged to a corresponding guide rod assembly 12 by inserting the tapered distal end 14a of the guiding portion 14 through the second implant opening 68. An elongated interconnecting member, such as rod 62, is preferably loosely connected to each of the connector assemblies 64. After being completely assembled, the implant assembly 60 is slidably advanced along the outer surface of the guiding portions 14 (as shown in solid lines), being guided along longitudinal axis L toward the bone screws 52. However, it should be understood that the implant assembly 60 can alternatively be partially assembled prior to being inserted into the patient's body, or the components of the implant assembly 60 can be individually inserted into the patient's body and assembled therein.

Notably, the guiding portions 14 of guide rod assemblies 12 can be reshaped or bent into other shapes or configurations which facilitate the advancement of the connector assemblies 64 and reduce the amount of interference or resistance between the connector assemblies 64 and the guiding portions 14. Additionally, if the connector assemblies 64 are not appropriately aligned with the bone screws 52, the guide rod assemblies 12 can be used as lever arms, providing additional leverage which aids in the bending or contouring of the spinal rod 62 to provide the proper alignment between the implant openings 68 and the shank portions 56. The guide rod assemblies 12 can also be used to urge or manipulate the bone screws 52 into alignment with the connector assemblies 64.

Referring to FIG. 4, the spinal implant 60 continues to be advanced along the guiding portions 14 and over the connecting portion 16 until disposed adjacent the vertebral column 50, with the shank portions 56 of the bone screws 52 disposed within the openings 68 in connector assemblies 64. The set screws 70 are then advanced through the threaded opening until each engages an outer surface of the rod 62, which in turn engages the connector assemblies 64 to the shank portions 56, to thereby fixedly attach the implant construct 60 to the bone screws 52. Once the implant assembly 60 is secured to the shank portions 56, the guide rod assemblies 12 are then separated from the bone screws 52 and removed from the patient's body.

It has thus been shown that one purpose of the guide rod assemblies 12 is to facilitate the loading of a spinal implant assembly 60, or other similar implants, onto a series of bone screws 52 engaged to the spinal column. The guiding portions 14 help guide the connector assemblies 64 into proper alignment with the bone screws 52 to allow subsequent engagement to the shank portions 56. Importantly, in order for the implant assembly 60 to be advanced along guiding portion 14 and across connecting portion 16, the maximum outer cross section of the guide rod assembly 12 must be sized to pass through the implant opening 68. To that end, the maximum outer diameter $D_m$ of the guide rod assembly 12 must be somewhat less than the inner diameter of the implant opening 68. It should also be apparent that another possible use of the guide rod assembly 12 is to drive or manipulate a bone screw 52. If the guide rod assembly is used as a driver or lever, the guiding portion 14 is preferably formed of a non-malleable or substantially rigid material, such as stainless steel or titanium, to avoid inadvertent bending. Additionally, it should be apparent that the guide rod assemblies 12 allow an implant construct, such as the implant assembly 60, to be assembled remote from the surgical site, and then delivered as a complete assembly to the surgical site. This decreases the number of implant components which must be manipulated by the surgeon inside the patient's body during a surgical procedure, thereby reducing the "fiddle factor" and the time spent in surgery.

If the guiding portions 14 are fabricated from a shape-memory material, such as nitinol, the guiding portions 14 can be easily returned to their original shape without having to manually bend the guiding portions 14 back into position.

If the bending or reshaping of the guiding portions 14 occurs at a temperature below the transformation temperature, the guiding portions 14 are returned to their pre-programmed or memorized shape by simply heating the shape-memory material to a temperature above the transformation temperature. Preferably, a shape-memory material having a transformation temperature slightly above normal body temperature is used to avoid the inadvertent return of the guiding portions to their memorized shape during the implant procedure. If the bending or reshaping occurs at a temperature somewhat above the transformation temperature, the guiding portions 14 are returned to their pre-programmed or memorized shape when the stress created by the lateral forces exerted on the guiding portions 14 by the implant assembly 60 are removed. Alternatively, if the guiding portions 14 are fabricated from aluminum or another similar malleable material, the guiding portions 14 can be manually bent back into their original shape. Once the guiding portions 14 are returned to their original configuration, the guide rod assemblies 12 can be reused to facilitate the loading of another implant assembly. Alternatively, the bent guide rod assemblies can be discarded as disposable, single use items.

Figure 5:
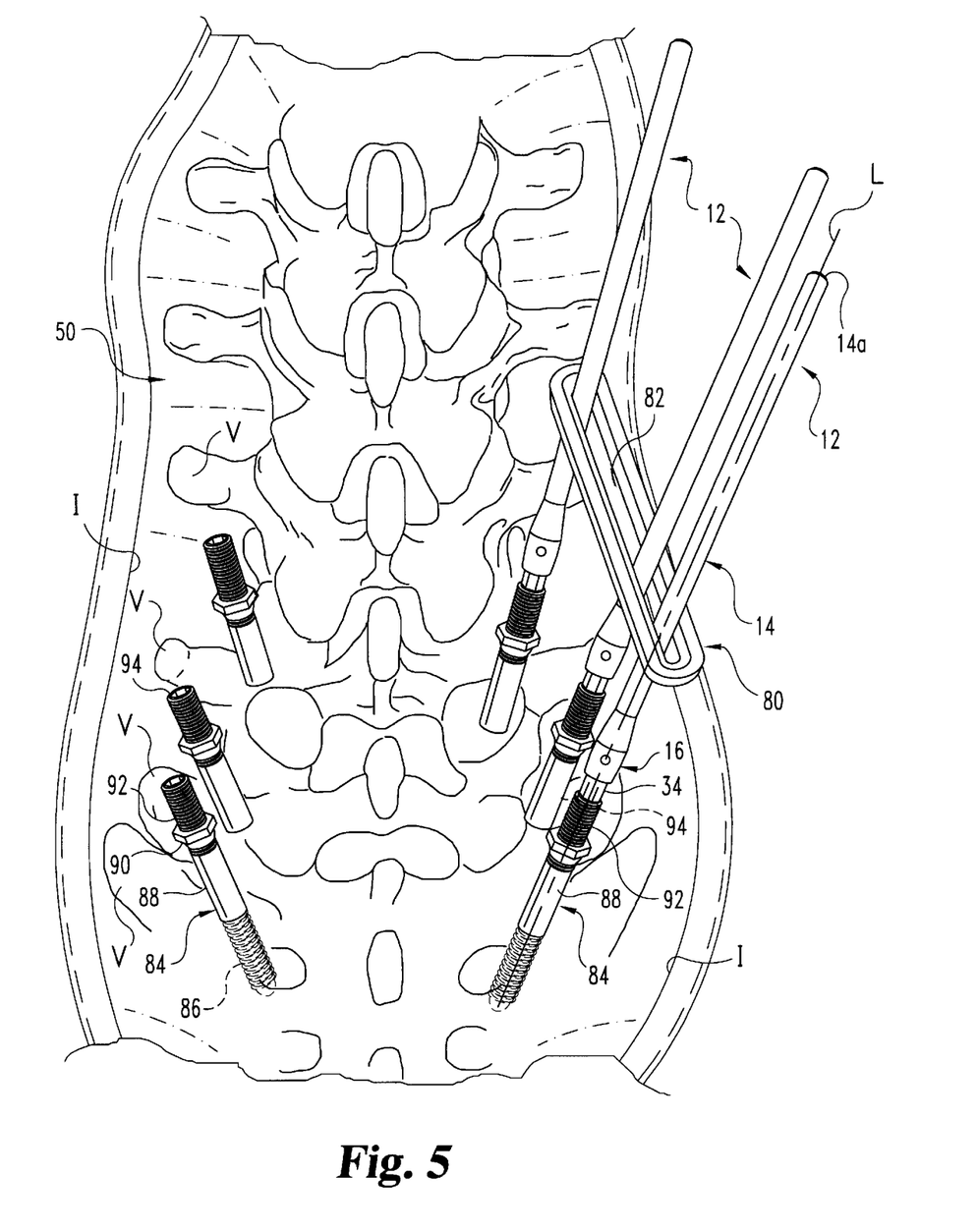
FIG. 5 is a posterior view of a vertebral column showing a number of bone screws attached thereto along each side of the vertebral column, a series of guide rod assemblies engaged to an exposed end portion of the bone screws, and a spinal plate engaged to the series of guide rod assemblies and being guided toward the exposed end portions of the bone screws.
Figure 6:
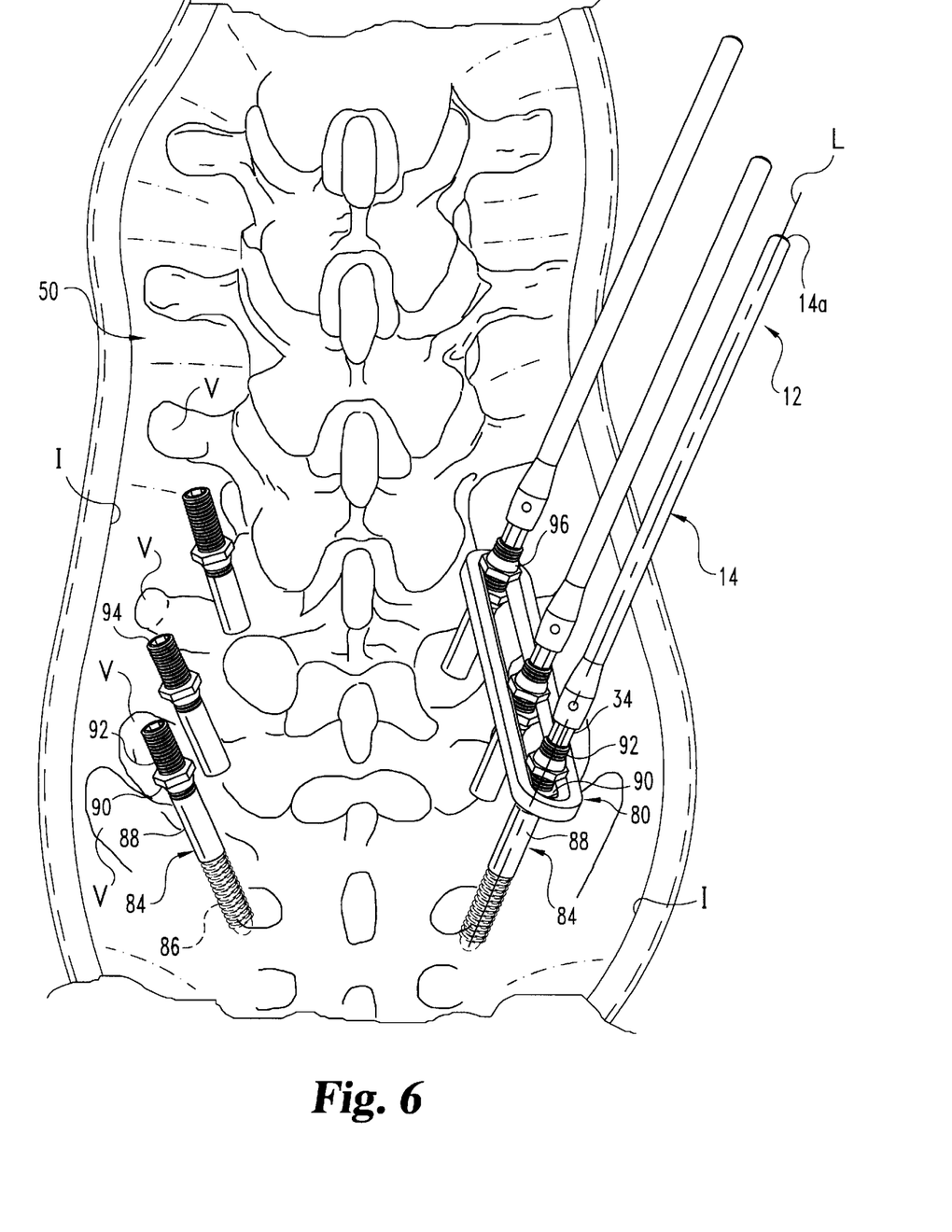
FIG. 6 is a posterior view of a vertebral column, showing the spinal plate engaged to the bone screws.

Referring now to FIGS. 5–6, shown therein is the guide rod assembly 12, as used in another application involving the guiding of an implant 80 from a location outside the body, remote from the surgical incision I, to a location adjacent the patient's spine. Referring specifically to FIG. 5, a number of bone anchors 84 are engaged to adjacent vertebrae V along each side of the vertebral column 50. In the illustrated embodiment, the bone anchors 84 are bone screws configured similar to bone screws 52, including a distal threaded portion 86 anchored in a corresponding vertebra V and a proximal shank portion 88 extending from the threaded portion 86 above a posterior surface of the vertebra. However, unlike bone screws 52, bone screws 84 have a threaded portion 92 having a plurality of machine threads cut along its length. Additionally, the bone screws 84 include a hub portion or lower nut 90 disposed along the shank portion 88. The shank portion 88 also defines a hexagonal-shaped opening or recess 94 corresponding to the shaped end portion 34 of the guide rod assembly 12.

In the illustrated embodiment, the implant 80 is a spinal plate having a length sized to span the distance between at least two adjacent vertebrae V. The spinal plate 80 includes a slot or opening 82 defined along its length and sized to slidably receive the threaded portion 92 of bone screw 84 therethrough. Further details regarding a similar spinal plate and bone screw are more fully described in U.S. Pat. No. 5,728,097 to Mathews, entitled "Method for Subcutaneous Suprafacial Internal Fixation", the contents of which are hereby incorporated by reference. It should be understood, however, that the precise configuration of the implant 80 and the bone screws 84 are for illustration purposes only, and that other configurations are also contemplated as being compatible for use with the present invention.

A series of guide rod assemblies 12 are releasably connected to the bone screws 84, with the hexagonal-shaped end portion 34 of the guiding portion 14 inserted within the hexagonally-shaped recess 94. In order to facilitate the loading of the spinal plate 80 onto the threaded portion 92 of the bone screws 84, the spinal plate 80 is engaged to the guide rod assemblies 12 by inserting the distal ends 14a of the guiding portions 14 through the opening 82. The spinal plate 80 is then slidably advanced along the outer surface of the guiding portions 14, being guided along longitudinal axis L toward the bone screws 84. The guiding portions 14 can be reshaped or bent into other shapes or configurations which facilitate the advancement of the spinal plate 80 by reducing the amount of interference or resistance between the spinal plate 80 and the guiding portions 14. Additionally, if the spinal plate 80 is not appropriately aligned with the bone screws 84, the guide rod assemblies 12 provide additional leverage which aids in providing the proper alignment between the openings 82 and the threaded portions 92. The guide rod assemblies can also be used to urge or manipulate the bone screws 84 into alignment with the spinal plate 80.

Referring to FIG. 6, the spinal plate 80 continues to be advanced along the guiding portions 14 and over the connecting portion 16 until disposed adjacent the vertebral column 50, with each of the threaded portions 92 extending through the opening 82, and the bottom of the spinal plate 80 disposed against the lower nut 90 of the bone screws 84. An upper nut 96 is then slid over the distal end 14a of each guiding portion 14 and slidably advanced along the longitudinal axis L until positioned adjacent the threaded portion 92. The spinal plate 80 is then securely engaged to the bone screws 84 by threading the upper nut 96 tightly against the upper surface of spinal plate 80. Once the spinal plate 80 is secured to the bone screws 84, the guide rod assemblies 12 are then separated from the bone screws 84 and removed from the patient's body.

Further embodiments of the present invention are described below and illustrated in the corresponding figures. It should be understood that the additional embodiments may be used interchangeably with guide rod assembly 12 in any of the applications described above to engage and guide an implant from a location outside the patient's body to a surgical site. It should also be understood that the elements or features of the disclosed embodiments are interchangeable. Thus, other embodiments of the present invention having combinations of features and elements different from those of the illustrated embodiments are also contemplated as being within the scope of the present invention.

Figure 7A:
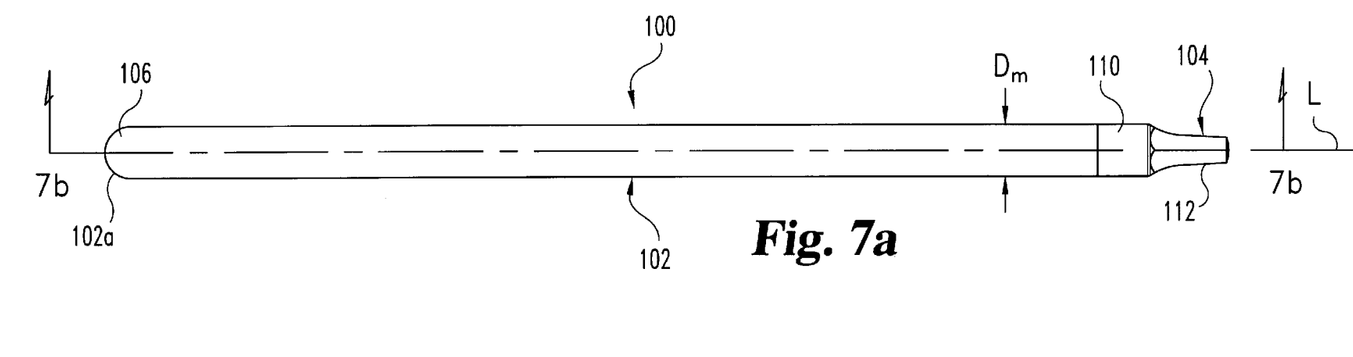
FIG. 7a is a side elevation view of a guide rod assembly according to another embodiment of the present invention.
Figure 7B:
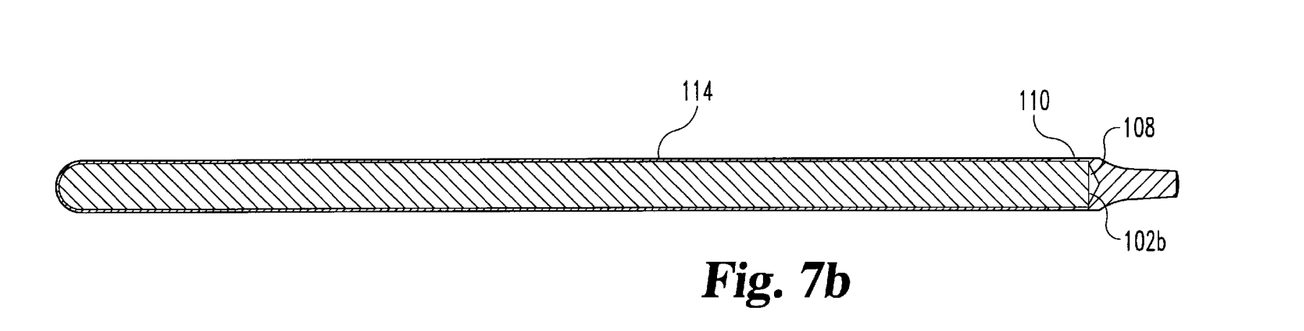
FIG. 7b is a cross sectional view of the guide rod assembly of FIG. 7a taken along line 7b—7b.

Referring to FIGS. 7a–7b, shown therein is a guide rod assembly 100 according to another embodiment of the present invention. Guide rod assembly 100 has a longitudinal axis L extending along an elongate guiding portion 102 and a connecting portion 104. Guiding portion 102 has a distal end 102a and a proximal end 102b, and can be formed of the same malleable and non-malleable materials discussed above with regard to guiding portion 14 of guide rod assembly 12. The distal end 102a is rounded to form a hemispherical dome 106, which facilitates the loading of an implant onto the guiding portion 102. The proximal end 102b is inserted within a longitudinal cavity 108 defined in connecting portion 104. The sidewall 110 surrounding cavity 108 is swaged or crimped onto the proximal end 102b to securely attach the guiding portion 102 to the connecting portion 104. Other methods of attaching guiding portion 102 to connecting portion 104 are also contemplated, such as, for example, by welding, threading or pinning.

The connecting portion 104 has a shaped end portion or stem 112 having a hexagonal shape; however, it should be understood that other shapes are also contemplated, such as those discussed above with regard to the shaped end portion 34 of guide rod assembly 12. Additionally, shaped end portion 112 is inwardly tapered to facilitate insertion into the shaped recess 59, 94 defined in bone screws 52, 84. The inward taper also serves as a wedge, aiding in retaining the engagement of the guide rod assembly 100 to the bone anchor. The outer surface of the guiding portion 102 is coated with a protective material 114. In one embodiment, the protective material 114 constitutes at least one layer of an elastomeric polymer, such as Teflon or the like. In the illustrated embodiment, the protective material 114 has a thickness that is substantially equal to the thickness of the side wall 110 to thereby provide a uniform outer cross section between the guiding portion 102 and the connecting portion 104. Preferably, the uniform outer cross section has a maximum outer diameter $D_m$ approximately equal to the diameter of the shank portion 56 of the bone anchor 52.

Figure 8:
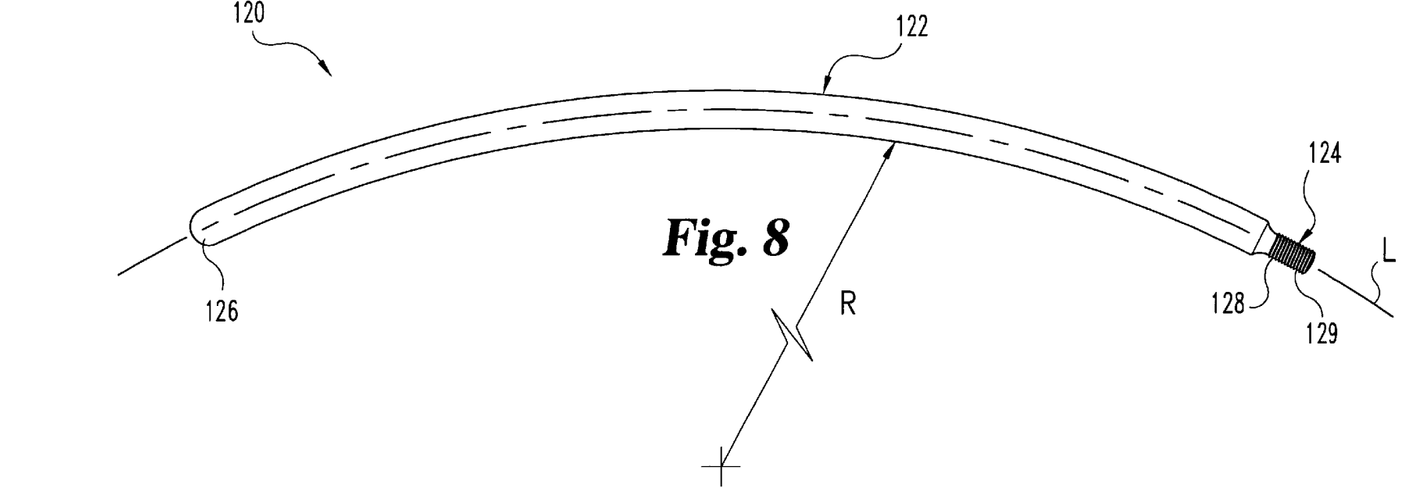
FIG. 8 is a side elevation view of a guide rod according to another embodiment of the present invention.

Referring to FIG. 8, shown therein is a guide rod 120 according to a further embodiment of the present invention. Guide rod 120 has a longitudinal axis L extending along an elongate guiding portion 122 and a connecting portion 124. Guide rod 120 is configured similar to guide rod assembly 100 in that it has a rounded end defining a hemispherical dome 126, and an opposite end defining a shaped end portion or stem 128. However, the shaped end portion 128 defines external machine threads 129, configured to engage internal threads defined in the bone anchor and aid in retaining the engagement of the guide rod assembly 100 to the bone anchor. Additionally, unlike guide rod assembly 100, the guiding and connecting portions 122, 124 are integral to guide rod 120, thus forming a single, unitary piece. Further, the guiding portion 122 has an arcuate shape.

Instead of manually bending or reshaping the guide rod 120 in preparation for an implant procedure, the guiding portion 122 is fabricated with a predetermined curvature, preferably a uniform radius R, suitable for guiding an implant along the longitudinal axis L. The guide rod 120 is engaged to the bone anchor, with the arcuate guiding portion 122 preferably extending outside of the body to a location laterally remote from the surgical site. In order to maintain the predetermined curvature and to avoid additional bending, the guiding portion 122 is preferably formed of a substantially rigid or nonmalleable material, such as, for example, stainless steel, titanium, or certain plastics. Guiding portion 122 can alternatively by formed of any malleable material, such as a soft aluminum, a shape-memory material, or certain compositions or formations of stainless steel or titanium to allow the guiding portion 122 to be reshaped into other shapes or configurations.

Figure 9:
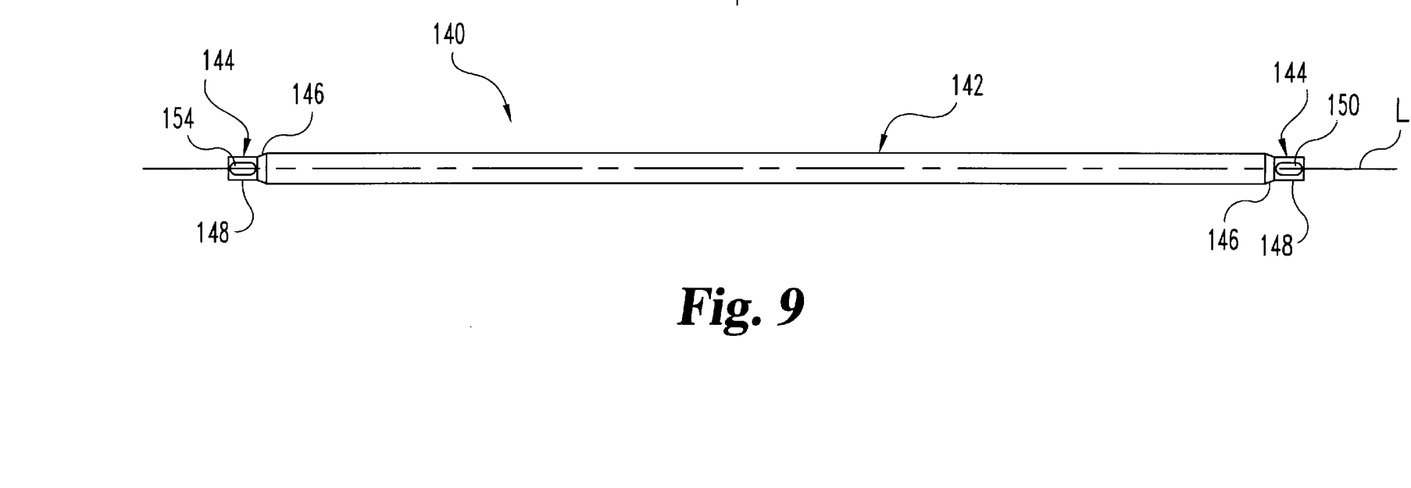
FIG. 9 is a side elevation view of a guide rod according to another embodiment of the present invention.

Referring to FIG. 9, shown therein is a guide rod 140 according to yet another embodiment of the present invention. Guide rod 140 has a longitudinal axis L extending along an elongate guiding portion 142 and integral connecting portions 144 disposed at opposite ends thereof. Guide rod 140 can be formed of the same malleable and nonmalleable materials discussed above with regard to guiding portion 14 of guide rod assembly 12. Each of the opposite connecting portions 144 has a tapered portion 146, serving as a transition between the guiding portion 142 and a shaped end portion 148. Shaped end portion 148 has a substantially circular shape with flat portions 150 stamped or machined onto opposite sides thereof that correspond to opposing sides of the hexagonal recess 58 defined in bone anchor 52. However, it should be understood that other shapes are also contemplated, such as those discussed above with regard to the shaped end portion 34 of guide rod assembly 12.

Figure 10A:
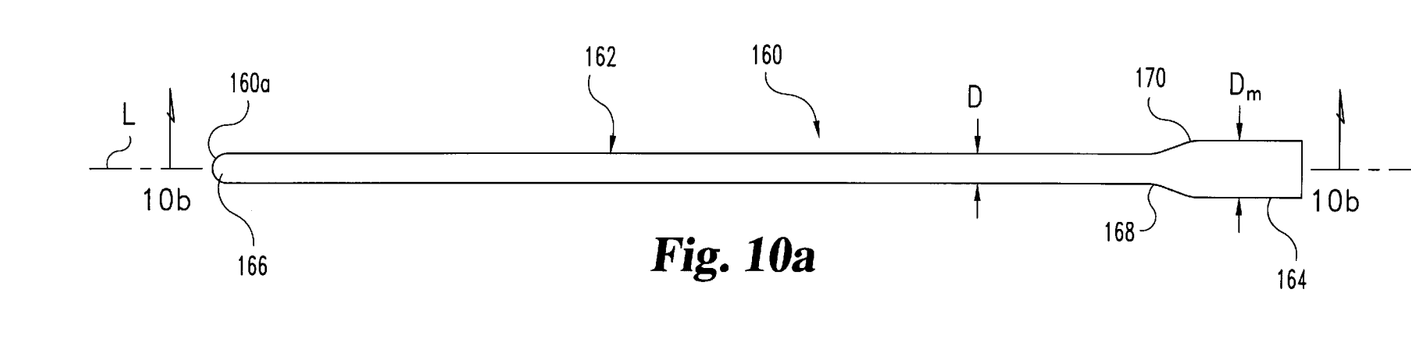
FIG. 10a is a side elevation view of a guide rod according to another embodiment of the present invention.
Figure 10B:
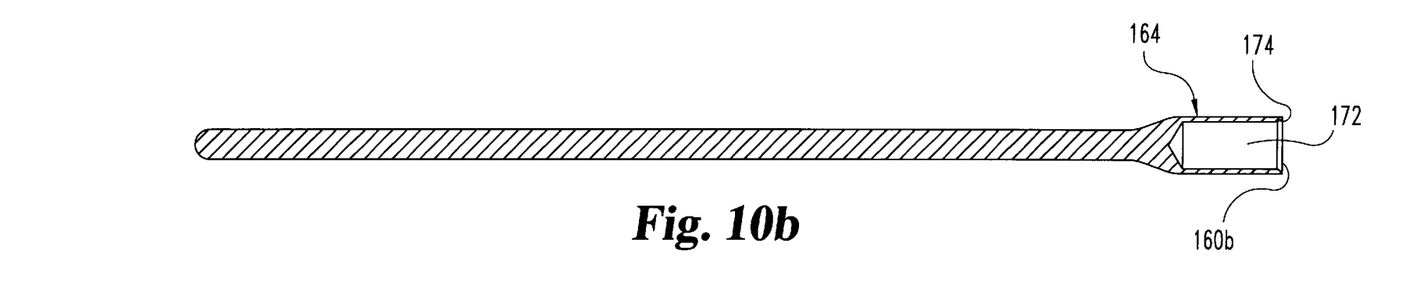
FIG. 10b is a cross sectional view of the guide rod of FIG. 10a taken along line 10b—10b.

Referring to FIGS. 10a–10b, shown therein is a guide rod 160 according to still another embodiment of the present invention. Guide rod 160 has a longitudinal axis L extending along an elongate guiding portion 162 and an integral connecting portion 164, and can be formed of any malleable or non-malleable material, such as, for example, those discussed above with regard to guiding portion 14 of guide rod assembly 12. The distal end 160a of guide rod 160 is rounded to form a hemispherical dome 166. The guiding portion 162 defines an outer diameter D, which smoothly transitions into connecting portion 164 having a maximum outer diameter $D_m$ by way of a circular fillet 168 and a circular round 170. The connecting portion 164 defines a shaped opening or recess 172 extending along longitudinal axis L and having an outward taper 174 opening onto the proximal end 160b of guide rod 160. The shaped recess 172 has a circular shape; however, other shapes are also contemplated as being within the scope of the invention.

Unlike the previous embodiments illustrated and described above, guide rod 160 is releasably engaged to the bone anchor 52 by sliding the connecting portion 164 over the shank portion 56 or other similar male drive geometry extending from the bone anchor 52. The outward taper 174 aids in guiding the connecting portion 164 over the shank portion 56. Preferably, the inner diameter of the recess 172 is sized slightly larger than the outer diameter of the shank portion 56 of bone anchor 52 to provide a secure engagement therebetween and to stabilize guide rod 160 during an implant procedure. The guide rod 160 effectively serves to extend the length of the shank portion 56, preferably to a location outside of the patient's body, and can be selectively detached or separated from the bone anchor 52 by simply removing the connecting portion 162 from the shank portion 156.

While the invention has been illustrated and described in detail in the drawings and foregoing description, the same is to be considered as illustrative and not restrictive in character, it being understood that only the preferred embodiments have been shown and described, and that all changes and modifications that come within the spirit of the invention are desired to be protected.

What is claimed is:

1. An instrument for guiding an implant to a location adjacent a bone anchor engaged to bone, comprising:

a longitudinal member having a connecting portion and a guiding portion, said connecting portion defining an end portion of said longitudinal member and adapted to releasably engage the bone anchor and being selectively separable therefrom, said guiding portion being adapted to engage the implant and guide the implant along a length of said guiding portion toward the bone anchor.

2. The instrument of claim 1 wherein said guiding portion is at least partially formed of a malleable material capable of being reshaped.

3. The instrument of claim 2 wherein said guiding portion is at least partially formed of a malleable material capable of being reshaped manually by hand.

4. The instrument of claim 2 wherein said malleable material is aluminum.

5. The instrument of claim 2 wherein said malleable material is a shape-memory material.

6. The instrument of claim 5 wherein said guiding portion has an initial configuration and a different reshaped configuration, said guiding portion being reshaped from said initial configuration to said different configuration at a temperature below the transformation temperature of said shape-memory material, and wherein said guiding portion is returned to said initial configuration upon heating said shape-memory material to said transformation temperature.

7. The instrument of claim 5 wherein said guiding portion has an initial configuration and a different reshaped configuration, said guiding portion being reshaped from said initial configuration to said different configuration through the imposition of stress at a temperature above the transformation temperature of said shape-memory material, and wherein said guiding portion is returned to said initial configuration upon removal of said stress.

8. The instrument of claim 1 wherein one of said bone anchor and said connecting portion includes a shaped end portion for engaging a corresponding shaped recess defined in another of said bone anchor and said connecting portion, said shaped end portion being engaged within said shaped recess to releasably connect said longitudinal member to said bone anchor.

9. The instrument of claim 8 wherein said shaped end portion and said shaped recess are each hexagonally-shaped.

10. The instrument of claim 8 wherein said shaped end portion is inwardly tapered.

11. The instrument of claim 8 wherein said shaped end portion and said shaped recess are each threaded, said shaped end portion capable of being threadedly engaged within said shaped recess to releasably connect said longitudinal member to said bone anchor.

12. The instrument of claim 1 wherein one of said connecting portion and said guiding portion defines a longitudinal cavity, and wherein an end portion of another of said connecting portion and said guiding portion being engaged within said cavity to attach said connecting portion to said guiding portion.

13. The instrument of claim 12 wherein said connecting portion and said guiding portion are attached by a cross pin disposed within an opening extending transversely through said longitudinal cavity and said end portion.

14. The instrument of claim 12 wherein said connecting portion and said guiding portion are attached by crimping said one of said connecting portion and said guiding portion defining said longitudinal cavity about said end portion of said another of said connecting portion and said guiding portion.

15. The instrument of claim 1 wherein said connecting portion and said guiding portion form a single unitary piece.

16. The instrument of claim I wherein the implant has an opening defined therethrough, said guiding portion and said connecting portion having an outer cross section sized to pass through said implant opening.

17. The instrument of claim 1 wherein said guiding portion has a second end portion extending outside the body when said guiding portion is engaged to said bone anchor.

18. The instrument of claim 1 wherein the implant includes:
 a longitudinal member having a length sized to span a distance between at least two of said bone anchors;
 at least two connectors, each of said connectors being configured to selectively engage the longitudinal member and a corresponding one of said bone anchors to operably connect said longitudinal member to said bone anchors, each of said connectors having an opening extending therethrough sized to slidably receive said guiding portion therein; and
 further comprising at least two of the instruments for guiding, each of the instruments being releasably engaged to a corresponding one of said bone anchors, said guiding portion of each of the instruments being inserted within a respective one of said openings to allow said implant to be slidably advanced along said guiding portions toward said at least two of said bone anchors.

19. The instrument of claim 18 further comprising means for selectively engaging each of said connectors to said longitudinal member and to said at least two of said bone anchors.

20. A bone anchor adapted to receive an implant, comprising:
 a bone engaging portion; and
 a detachable extension portion extending along a longitudinal axis and having an end portion adapted to releasably engage said bone engaging portion and being selectively separable therefrom, said extension portion having an outer cross section sized to slidably receive the implant thereon and guide the implant along the longitudinal axis to a location adjacent said bone engaging portion.

21. The bone anchor of claim 20 wherein said extension portion has a predetermined arcuate shape.

22. The bone anchor of claim 20 wherein one of said bone engaging portion and said extension portion defines an opening and another of said bone engaging portion and said extension portion defines a stem, said stem being engaged within said opening to releasably connect said extension portion to said bone engaging portion, said extension portion being detachable from said bone engaging portion by selectively removing said stem from said opening.

23. The bone anchor of claim 22 wherein said bone engaging portion defines said opening and said extension portion defines said stem, said opening and said stem each having a corresponding shape.

24. The bone anchor of claim 22 wherein said bone engaging portion defines said stem and said extension portion defines said opening, said opening being substantially circular and being sized to receive said stem therein.

25. The bone anchor of claim 20 wherein said extension portion is at least partially formed of a shape-memory material; and
 wherein said extension portion has an initial configuration and a different reshaped configuration, said extension portion being reshaped from said initial configuration to said different configuration at a temperature below the transformation temperature of said shape-memory material; and
 wherein said extension portion is returned to said initial configuration upon heating said shape-memory material to said transformation temperature.

26. The bone anchor of claim 20 wherein said extension portion is at least partially formed of a shape-memory material; and
 wherein said extension portion has an initial configuration and a different reshaped configuration, said extension portion being reshaped from said initial configuration to said different configuration through the imposition of stress at a temperature above the transformation temperature of said shape-memory material; and
 wherein said extension portion is returned to said initial configuration upon removal of said stress.

27. The bone anchor of claim 20 wherein the implant has a passage extending therethrough, said passage being sized to slidably receive said extension portion therein to allow the implant to be slidably advanced along a length of said extension portion toward said bone engaging portion.

28. The bone anchor of claim 20 wherein said extension portion has a second end portion disposed outside of the body when said extension portion is engaged to said bone engaging portion.

29. The bone anchor of claim 28 wherein said extension portion is oriented substantially perpendicular to said bone engaging portion.

30. The bone anchor of claim 20 wherein said extension portion is covered with at least one layer of a protective coating selected from the group consisting of an anodized oxide film or an elastomeric polymer.

31. A spinal fixation system, comprising:
 a bone anchor having means for engaging a portion of the spine;
 a spinal implant;
 means for guiding said spinal implant from a first location outside the body to a second location proximately adjacent said bone anchor; and
 means for releasably engaging said guiding means to said bone anchor, said engaging means allowing said guiding means to be selectively removed from said bone anchor.

32. The system of claim 31 wherein said guiding means is at least partially formed of a shape-memory material; and
   wherein said guiding means is capable of being reshaped from an initial configuration to a different configuration at a temperature below the transformation temperature of said shape-memory material; and
   wherein said guiding means returns to said initial configuration upon heating said shape-memory material to said transformation temperature.

33. A method for guiding an implant, comprising:
   providing a bone anchor having a bone engaging portion and a detachable guiding portion releasably connected to the bone engaging portion and being selectively separable therefrom;
   anchoring the bone engaging portion to a patient's spine;
   engaging the implant to the detachable guiding portion;
   advancing the implant along the detachable guiding portion toward the bone engaging portion until the implant is positioned proximately adjacent the bone engaging portion;
   separating the detachable guiding portion from the bone engaging portion; and
   removing the detachable guiding portion from the patients body.

34. The method of claim 33 wherein the implant is guided from a location outside the patient's body to a location adjacent the patient's spine.

35. The method of claim 33 further including releasably connecting the detachable guiding portion to the bone engaging portion after anchoring the bone engaging portion to the patient's spine.

36. The method of claim 33 wherein one of the guiding portion and the bone engaging portion defines an opening and another of the guiding portion and the bone engaging portion includes a stem, the stem being engaged within the opening to releasably connect the guiding portion to the bone engaging portion; and
   wherein the separating includes removing the stem from the opening.

37. The method of claim 36 wherein the stem and the opening are each threaded, the stem being threadedly engaged within the opening to releasably connect the guiding portion to the bone engaging portion; and
   wherein the separating includes unthreading the stem from the opening.

38. The method of claim 33 wherein the guiding portion is at least partially formed of a malleable material; and
   further comprising bending the guiding portion from an initial configuration to a reshaped configuration suitable for advancing the implant along the guiding portion.

39. The method of claim 38 wherein the bending of the guiding portion occurs prior to the advancing of the implant along the guiding portion.

40. The method of claim 38 wherein the bending is performed manually by hand.

41. The method of claim 38 wherein the guiding portion is oriented substantially perpendicular to the bone engaging portion when the guiding portion is in the reshaped configuration.

42. The method of claim 38 wherein the bending of the guiding portion occurs during the advancing of the implant along the guiding portion.

43. The method of claim 38 wherein the guiding portion is at least partially formed of a shape-memory material; and
   wherein the bending occurs at a temperature below the transformation temperature of the shape-memory material; and
   further comprising heating the shape-memory material to the transformation temperature and returning the guiding portion to the initial configuration.

44. The method of claim 38 wherein the guiding portion is at least partially formed of a shape-memory material; and
   wherein the bending occurs through the imposition of stress onto the guiding portion at a temperature above the transformation temperature of the shape-memory material; and
   further comprising removing the stress and allowing the guiding portion to return to the initial configuration.

45. The method of claim 33 wherein the implant has an opening defined therethrough; and
   wherein the engaging includes inserting the guiding portion through the implant opening; and
   wherein the advancing includes sliding the implant along an outer surface of the guiding portion.

46. The method of claim 33 wherein the bone engaging portion of the bone anchor includes a threaded portion and a driving portion, the guiding portion having an end portion adapted to releasably engage the driving portion; and
   wherein the anchoring includes releasably engaging the end portion to the driving portion and driving the threaded portion into a vertebral body.

47. The method of claim 33 further comprising:
   providing at least two of the bone anchors, each having a bone engaging portion and a detachable guiding portion;
   anchoring the bone engaging portions to the patient's spine;
   engaging the implant to each of the detachable guiding portions;
   advancing the implant along the detachable guiding portions toward the bone engaging portions until the implant is positioned proximately adjacent the bone engaging portions;
   separating the detachable guiding portions from the bone engaging portions; and
   removing the detachable guiding portions from the patient's body.

48. The method of claim 47 further comprising:
   providing an implant including:
      a longitudinal member having a length sized to span a distance between the bone anchors, and
      at least two connectors, each of the connectors being configured to selectively engage the longitudinal member and a corresponding one of the bone engaging portions to operably connect the longitudinal member to the bone anchors;
   engaging the connectors to the longitudinal member;
   slidably engaging the connectors to the detachable guiding portions; and
   slidably advancing the connectors along the detachable guiding portions toward the bone engaging portions until the implant is positioned proximately adjacent the bone engaging portions.

49. The method of claim 48 wherein each of the connectors has an opening extending therethrough being sized to slidably receive a corresponding one of the guiding portions therein to allow the connectors to be advanced along the guiding portions toward the bone engaging portions.

50. The method of claim 48 further comprising provisionally engaging the connectors to the longitudinal member outside of the patient's body prior to advancing the implant along the guiding portions toward the bone engaging portions.

* * * * *